(12) United States Patent
Rau

(10) Patent No.: US 6,310,014 B1
(45) Date of Patent: Oct. 30, 2001

(54) PERSONAL AND HOUSEHOLD CARE COMPOSITIONS

(75) Inventor: Allen H. Rau, Cincinnati, OH (US)

(73) Assignee: Phyzz Inc., Cincinnati, OH (US)

( * ) Notice: Subject to any disclaimer, the term of this patent is extended or adjusted under 35 U.S.C. 154(b) by 0 days.

(21) Appl. No.: 09/412,516

(22) Filed: Oct. 5, 1999

(51) Int. Cl.⁷ .............................. C11D 17/00; C11D 3/22; A61K 7/00; B08B 7/00
(52) U.S. Cl. .................... 510/108; 510/130; 510/135; 510/137; 510/138; 510/159; 510/276; 510/278; 510/338; 510/400; 510/407; 510/437; 510/441; 510/470; 424/401; 134/42
(58) Field of Search .................... 510/130, 108, 510/135, 137, 159, 138, 276, 278, 338, 349, 400, 407, 437, 441, 470; 424/401, 466, 44; 134/42

(56) References Cited

U.S. PATENT DOCUMENTS

| 3,012,893 | 12/1961 | Kremzner et al. | 426/572 |
|---|---|---|---|
| 3,316,691 | * 5/1967 | Sesny et al. | 502/60 |
| 3,947,566 | 3/1976 | Sarna et al. | 424/45 |
| 3,947,567 | 3/1976 | Berg, Jr. et al. | 424/45 |
| 3,947,568 | 3/1976 | Bates et al. | 424/47 |
| 3,985,909 | 10/1976 | Kirkpatrick | 426/572 |
| 3,985,910 | 10/1976 | Kirkpatrick | 426/572 |
| 4,001,457 | 1/1977 | Hegadorn | 426/572 |
| 4,263,328 | * 4/1981 | Parada et al. | 426/103 |
| 4,289,794 | 9/1981 | Kleiner et al. | 426/660 |
| 4,574,052 | 3/1986 | Gupte et al. | 510/120 |
| 4,592,855 | * 6/1986 | Gioffre et al. | 510/117 |
| 4,837,039 | 6/1989 | Gallart et al. | 426/572 |
| 4,952,417 | 8/1990 | Gallart et al. | 426/572 |
| 5,165,951 | * 11/1992 | Gallart et al. | 426/572 |
| 5,279,842 | * 1/1994 | Gallart et al. | 426/282 |

FOREIGN PATENT DOCUMENTS

| 0349314 | * | 1/1990 | (EP) . |
|---|---|---|---|
| 2050410 | * | 1/1981 | (GB) . |
| 07082103 | * | 3/1995 | (JP) . |
| 9615815 | * | 5/1996 | (WO) . |
| 9924547 | * | 5/1999 | (WO) . |

\* cited by examiner

*Primary Examiner*—Lorna M. Douyon
(74) *Attorney, Agent, or Firm*—Piper Marbury; Rudnick & Wolfe, LLP; Steven B. Kelber, Esq.

(57) ABSTRACT

Personal and household care compositions that deliver an audible crackling or popping sound during use. The sound is created by the release of pressurized carbon dioxide that has been encapsulated in a water-soluble structure. The carbon dioxide gas is released as the encapsulating material dissolves or when it is ruptured by mechanical action. The popping or crackling sound helps create consumer interest by signaling the presence and continued action of the product.

12 Claims, No Drawings

PERSONAL AND HOUSEHOLD CARE COMPOSITIONS

BACKGROUND OF THE INVENTION

1. Field of the Invention

This invention pertains to personal and household care products that include a gasified solid. The gasified solid provides a popping, crackling, or sizzling sound during product use. If the product is used on the skin, the gasified solid also provides a tingling sensation. The sound and/or tingle indicates the presence and continued action of the product.

2. Background of the Prior Art

Many types of personal and household care products are known and used every day by consumers. These products include items such as skin cleaners, moisturizers, bath additives, rug cleaners, room fresheners, and laundry detergents. Many other products, of course, fit into these general categories.

In the past, developers of consumer products determined that a consumer is generally more satisfied if more than one sense is involved in the use of a product. This is why fragrance is added to personal care and household products, why food manufacturers pay so much attention to product taste and texture, why a variety of colors and appearances are available for most cosmetic items, and why package design is such an important feature in a product's marketability.

For example, many of the personal and household care products of today stimulate the sense of smell through the use of perfumes. Interesting colors are utilized in products in order to stimulate the sense of sight. Warming sensations or texture is incorporated into the product or some attribute of its performance (e.g., foam) to stimulate the sense of feel. However, the sense of hearing is rarely, if ever, stimulated by the personal and household care products of today.

The present invention fills that void by allowing the sense of hearing to be stimulated by many everyday products.

U.S. Pat. Nos. 4, 289,794; 3,012,893; 3,985,909; 3,985,910; 4,001,457; 4,837,039; 4,952,417, and 5,165,842 disclose processes that may be germane to the process for the preparation of a gasified material. Each of these patents are incorporated by reference herein. The products disclosed in the above-identified patents are products that are intended for use as a candy. These products provide a sensation of popping and crackling when they are placed in the mouth. The popping sensation is caused by the release of carbon dioxide when the candy is dissolved in the mouth or the carbon dioxide bubbles are ruptured by chewing. There is no discussion or suggestion of using a gasified solid in personal or household care products.

U.S. Pat. No. 4,574,052 discloses a crackling aerosol foam. In this invention, a crackling sound is created when an absorbed liquefied gas (i.e., zeolite or a molecular sieve) is released from the pressure of an aerosol container. However, the present invention does not require the use of pressurized packaging, which is beneficial because it reduces the possibility of the product exploding and potentially causing damage. Further, the present invention does not demand that the gas be liquified.

U.S. Pat. Nos. 3,947,566, 3,947,567, and 3,947,568 describe effervescent compositions in which bubbles are created by releasing liquefied gas from the pressure of an aerosol package. In the present invention, neither pressurized packaging nor liquified gas is required.

SUMMARY OF THE INVENTION

It is an object of this invention to provide personal and household care products that contain a gasified solid. The gasified solid provides a popping, crackling, or sizzling sound during product use, and, if used on the skin, also provides a tingling sensation.

A water soluble material, hereinafter referred to as a "gasified solid", encapsulates carbon dioxide into a solid matrix of sugar, glucose, and lactose. This matrix can hold tiny pockets of carbon dioxide gas at pressures exceeding several hundred pounds per square inch. When the water soluble material is placed in water, thereby dissolving the solid structure, or when the water soluble material is mechanically abraded, thereby rupturing the solid matrix structure, the pressurized gas is released with a popping sound.

Generally, personal care products are items or compositions used by an individual to clean and/or moisturize the body. Some personal care products possible within this invention include crackling bath additives and skin cleansers that make a popping noise during use.

Household care products are items or compositions used by an individual to clean and/or deodorize a house or items within a house. Some possible household care products included within this invention are crackling laundry detergents, dish and hard surface detergents, and rug cleaners that make a popping sound when walked upon.

A primary benefit of this technology is that the popping, crackling, or sizzling sound generated by the rupturing of the gasified solid can be used as an indicator of the presence and continued action of the product. Additionally, the sound generated stimulates the sense of hearing to aesthetically please the consumer and further creates an impression of an improved use of the product.

A secondary benefit of this technology is that when products containing gasified solids are used in contact with the skin, a tingling sensation can be felt. This sensation creates an impression of an improved cleansing or softening of the skin.

A third benefit of this technology is that pressurized packaging is not required. This reduces the possibility of the product exploding and causing damage.

DETAILED DESCRIPTION OF THE INVENTION

The purpose of the present invention is to include a gasified solid into personal and household care products. The key components of the invention are a gasified solid and an anhydrous base, which can be either liquid or solid. The present invention can further incorporate additional materials that give the product its particular function.

The gasified solid component is a water soluble material that encapsulates bubbles of pressurized carbon dioxide. When this material contacts water or is mechanically ruptured, the encapsulated carbon dioxide is rapidly released, thereby creating a popping sound. The water soluble material can be prepared by the methods described in U.S. Pat. Nos. 4,289,794, 3,012,893, 3,985,909, 3,985,910, 4,001,457, 4,837,039, 4,952,417, 5,165,951 and 5,279,842. Other methods of manufacturing substantially similar materials may also be possible for use in this invention.

A preferred water soluble material is a blend of sugar, glucose, and lactose. However, other materials could be used to encapsulate the pressurized gas. For example, compositions prepared using alternate materials that provide the same function would be useful in this invention. Examples of alternative matrices include water soluble polymers such as polyethylene glycols (PEG) and polyvinyl alcohols (PVA) as well as blends of these with waxes, e.g. parafin.

It is conceivable that gases other than carbon dioxide could be encapsulated in the water soluble matrix. One example where desirable, is nitrogen gas. Non-poisonous, non-reactive gases such as the noble gases (e.g. helium, argon) could also be used. Likewise, these compositions would be useful in the present invention. Volatile fragrance components are also desirably used to stimulate an additional sense.

The composition of the anhydrous base depends on the physical form and intended function of the product. Some general guidelines are set forth below.

For solid products, the base can include anhydrous materials such as salts (including, but not limited to, organic or inorganic chlorides, sulfates, sulfites, carbonates, bicarbonates, iodides, citrates, and the like), mineral powders such as (but not limited to) talc, kaolin, silica, silicates, and iron oxide, carbohydrates such as (but not limited to) sugars, starches, and maltodextrins, polymers such as (but not limited to) polyethylene, polypropylene and polystyrene, and proteins such as (but not limited to) keratin and collagen. Throughout this application, examples are not intended as limiting, unless so indicated.

Liquid products are generally suspensions of the gasified solid. The liquid phase must be virtually anhydrous to prevent premature dissolution of the gasified solid. As used herein, "virtually anhydrous" indicates that the component or product contains water in an amount of no more than about 1% by weight. Illustrative examples of the liquid phase include, but are not limited to, mineral oils, vegetable oils (such as corn oil, avocado oil, and safflower oil), petrolatum, liquid fatty acid esters (such as isopropyl palmitate, $C_{12-15}$ alcohols benzoate, and isopropyl myristate), silicone derivatives (such as cyclomethicone, dimethicone, and silicone oil), glycerin, propylene glycol, butylene glycol, low molecular weight polyethylene glycols, and alcohols (such as ethanol, isopropanol, and butanol).

Additionally, anhydrous functional materials can be added to either liquid or solid products within the scope of this invention. Some examples include surfactants, emollients, humectants, polymers, enzymes, builders, insecticides, and sun screens.

Without intending to offer a complete list, some typical anhydrous surfactants that can be used in the present invention include the following anionic, cationic, nonionic and amphoteric materials: sodium cocoyl isethionate, sodium dodecyl benzene sulfonate, sodium methyl oleoyl taurate, sodium lauryl sulfoacetate, sodium lauryl sulfate, sodium $C_{14-16}$ olefin sulfonate, disodium lauryl sulfosuccinate, cocamidopropyl betaine, lauramide MEA, sucrose stearate, cetyl alcohol, laureth-3, polysorbate-85, sorbitan monolaurate, PEG-30 Castor Oil, nonoxynol-9, PEG-6 cocamide, and distearyl dimethyl ammonium chloride.

Representative emollients that can be used in the present invention include mineral oils, vegetable oil, petrolatum, dimethicone, dimethicone copolyols, cyclomethicone, silicone oils and waxes, fatty acid esters, and fatty alcohols.

Representative anhydrous humectants for inclusion in the present invention include polyethylene glycols, glycerin, propylene glycol, sorbitol, and sodium lactate.

Potential polymers that can be incorporated into the present invention include polyquaternium 10, methyl cellulose, cellulose, hydroxymethyl cellulose, guar gum, xanthan gum, polyethylene, polypropylene, and polystyrene.

Enzymes may also be incorporated into the personal and household care products of the present invention. Examples of enzymes that may be incorporated include protease, amylase, cellulase, and lipase.

Builders include sodium citrate, sodium polyphosphate, sodium phosphate, and zeolite.

An insect repellant such as DEET or citronella could also be incorporated into the present invention to add a further advantage of repelling insects.

Sun screens such as octyl methoxycinnimate, PABA, homosalate, and benzophenone-3 can be considered for inclusion in the products of the present invention to add the desired quality of protection from harmful UV rays.

Cosmetic additives such as colorants and fragrances can, of course, be included at the formulator's discretion to enhance the aesthetic qualities of the products of the present invention.

It is important to note that products that incorporate a sugar-based gasified solid such as in the present invention are virtually anhydrous to prevent dissolution of the solid matrix. However, if appropriately formulated, the products formed can be either solid or liquid.

It is also important to note that pressurized packaging such as aerosol cans are not needed in the present invention. This is beneficial in that it reduces the risk of explosion during shipping, storage, or use.

The following prototypical formulations, both solid and liquid, illustrate the versatility of this invention.

I. Crackling Foaming Bath Powder

| Material | % (w/w) |
| --- | --- |
| Sodium sulfate | 74.0 |
| Sodium methyl oleoyl taurate | 5.0 |
| Sodium sulfoacetate | 2.0 |
| Maltodextrin | 6.0 |
| Gasified solids | 10.0 |
| Fragrance | 3.0 |
| Colorant | As desired |
| Total | 100.0 |

The bath powder was made by adding fragrance to the maltodextrin and mixing with a planetary mixer until the composition was uniform. Next, all of the remaining materials except for the gasified solids were added to the mixer and stirred until the resulting composition was uniform. The gasified solids were then added and mixed until a uniform composition was achieved. Next, 25 grams of the resulting product was added to 20 liters of 40° C. water running at approximately 6 liters/minute. Dense foam was formed and a crackling noise could be heard for about 4 minutes.

II. Crackling Bath Granules

| Material | % (w/w) |
| --- | --- |
| Gasified solids | 10.0 |
| Sodium sulfate | 4.00 |
| Fragrance | 0.05 |
| Colorant | 0.22 |
| Total | 100.00 |

The bath granules were prepared by first adding fragrance and color to sodium sulfate and mixing the composition with a planetary mixer until it was uniform. The gasified solids were then added and the composition was mixed until it was uniform. 25 grams of the resulting product was then added to 20 liters of 40° C. water. The resulting bath water was colored and fragranced. A crackling noise could be heard for approximately 4 minutes.

III. Effervescent Foaming Cracking Bath Granules

| Material | % (w/w) |
|---|---|
| Gasified solids | 10.0 |
| Foaming Effervescent Granules* | 90.0 |
| Total | 100.0 |

*Composition of Foaming Effervescent Granules:

| | |
|---|---|
| Citric acid | 37.1 |
| Sodium bicarbonate | 18.6 |
| Sodium carbonate | 18.6 |
| Maltodextrin | 17.7 |
| Sodium methyl oleoyl taurate | 5.0 |
| Sodium lauryl sulfoacetate | 2.0 |
| Fragrance | 1.0 |
| Colorant | As desired |
| Total | 100.0 |

First, the foaming effervescent granules were prepared by adding fragrance to the maltodextrin and mixing the composition with a planetary mixer until it was uniform. Next, the remaining materials were added to the mixer and stirred until the resulting composition was uniform. This mixture was then compacted on a standard roll compactor and screened. The portion caught on a 10-mesh screen was retained for use in this prototype as effervescent granules.

Next, the gasified solids were mixed with the effervescent granules until the composition was uniform. 25 grams of the resulting product was then added to 20 liters of 40° C. water running at about 6 liters/minute. Dense foam was formed and a crackling noise could be heard for about 4 minutes.

IV. Crackling Footsoak Granules

| Material | % (w/w) |
|---|---|
| Gasified solids | 10.0 |
| Effervescent Footsoak Granules* | 90.0 |
| Total | 100.0 |

| | |
|---|---|
| *Composition of Effervescent Footsoak Granules: | 39.5 |
| Citric acid | 39.5 |
| Sodium bicarbonate | 20.0 |
| Sodiumcarbonate | 20.0 |
| Maltodextrin | 18.6 |
| Fragrance | 1.0 |
| PEG-30 Castor Oil | 0.4 |
| Menthol | 0.5 |
| Colorant | As desired. |
| Total | 100.0 |

The effervescent footsoak granules were prepared by dissolving the methanol in the fragrance and then mixing the composition with the PEG-30 castor oil. This blend was then added to the maltodextrin and mixed using a planetary mixer until the composition was uniform. Next, the remaining materials were added to the mixer and stirred until the resulting composition was uniform. This mixture was then compacted on a standard roll compactor and screened. The portion that passed through a 10-mesh screen and was caught on a 40-mesh screen was retained for use in this prototype as footsoak granules.

Next, the gasified solids were mixed with the effervescent footsoak granules until the composition was uniform. 25 grams of the resulting product was then added to 10 liters of 40° C. water. A crackling noise could be heard for about 4 minutes.

V. Crackling Laundry Detergent

| Material | % (w/w) |
|---|---|
| Gasified solids | 15.0 |
| Commercial Laundry Detergent* | 85.0 |
| Total | 100.0 |

*Approximate composition of Commercial Laundry Detergent:

| | |
|---|---|
| Sodium carbonate | 40.0 |
| Sodium tripolyphosphate | 20.0 |
| Cellulose gum | 1.0 |
| Hydrated silica | 5.0 |
| Linear alkyl benzene suffonate | 1.0 |
| $C_{14-15}$ alcohol ethoxylate (7 mole) | 20.0 |
| Nonoxynol-4 | 10.0 |
| Sodium sulfate | 3.0 |
| Optical brightener | Less than 1.0 |
| Total | 100.0 |

First, the commercial laundry detergent was blended with the gasified solids using a planetary mixer until the composition was uniform. Next, three ounces of the resulting mix was placed in a standard washing machine while it was filling with water. Popping noises were heard for several minutes.

VI. Popping Warming Facial Cleanser

| Material | % (w/w) |
|---|---|
| $C_{12-15}$ alcohols benzoate | 33.4 |
| Sodium methyl oleoyl taurate | 8.3 |
| Zeolite | 13.3 |
| Gasified solids | 44.0 |
| Fragrance | 1.0 |
| Total | 100.0 |

First, the surfactant, fragrance, and zeolite were blended into the liquid ester using a conventional mixer. The gasified solids were then stirred into this mixture. The resulting composition (i.e., popping warming facial cleaner) was evaluated by placing a few grams of the composition on wet hands and massaging the composition on the face. Popping noises, faint tingling, and warming due to the zeolite were noticeable. The sound is attributed to both the dissolution of the gasified solid and to its rupture from massaging action on the face.

VII. Popping Warming Hand Cleaner

| Material | % (w/w) |
|---|---|
| $C_{12-15}$ alcohols benzoate | 30.0 |
| Sodium methyl oleoyl taurate | 9.0 |
| Zeolite | 15.0 |
| Gasified solids | 45.0 |
| Fragrance | 1.0 |
| Total | 100.0 |

The surfactant, fragrance, and zeolite were blended into the liquid ester using a conventional mixer. Next, the gasified solids were stirred into the composition. This composition (i.e. popping warming hand cleaner) was evaluated by placing a few grams of the composition on wet hands and rubbing them together. Popping noises, faint tingling, and warming due to the zeolite were noticeable.

VIII. Crackling Salt Rub

| Material | % (w/w) |
| --- | --- |
| Gasified solids | 6.0 |
| Commercial Salt Rub* | 94.0 |
| Total | 100.0 |

*Approximate composition of Commercial Salt Rub:
| | |
| --- | --- |
| Sodium chloride | 80.0 |
| Cyclomethicone | 20.0 |
| Total | 100.0 |

The gasified solids were blended directly into the Commercial Salt Rub product. The resulting product was then rubbed on the skin in the shower to exfoliate dead skin. Popping sounds could be heard and a faint tingling sensation was felt on the skin.

IX. Crackling Body or Hand Wash

| Material | % (w/w) |
| --- | --- |
| PEG-6 cocamide | 50.0 |
| Dimethicone copolyol | 18.0 |
| Sodium cocoyl isethionate | 7.0 |
| PEG-180 | 5.0 |
| Gasified solids | 20.0 |
| Fragrance, Color | As desired |
| Total | 100.0 |

The PEG-6 cocamide, dimethicone copolyol and PEG-180 were mixed in a heated mixer. Next, the temperature of the mix was raised to a temperature above the melt point of the PEG-180 (i.e., to approximately 65° C.) The mixture was then allowed to cool with stirring to about 30° C. The remaining ingredients were then added with mild stirring. The product is a gel that foams copiously when used as a hand wash. Crackling can be heard almost immediately upon dilution with water.

This invention encompasses within its scope applications that do not require a water soluble matrix, although the same may be used. Low melting point temperature coatings, such as fatty acid esters (e.g. glyceryl, propylene glycol, sorbitan and others) may be used to form the matrix for the gasified solid. In the alternative, such coatings (e.g. cocoa butter, PEG, stearic acid, wax, etc.) may be used to coat or encapsulate the sugar-based matrix gasified solids. One example of this aspect of the invention is a combination of gasified solids with flame colorants suitable for use in a fireplace. These colorants alter the color of the flames, and if combined with a gasified solid with a low melting point matrix, will provide an enhanced popping sound as well. Colorants include lithium salts like lithium chloride, and similar salts of boron, sodium, calcium, copper, potassium, strontium, indium and barium. Thus, in its broadest aspect, this invention comprises a mixture of gasified solids, which release the trapped gas under conditions of use, and an active agent having at least one function under the same conditions of use.

In net, it is felt that the addition of gasified solids to personal and household products gives the novel and unobvious benefit of allowing these products to emit a popping, crackling, or sizzling sound during use. This sound signals the consumer that the product is present and is working. Further, the sound emitted gives the consumer the impression of an enhanced effectiveness of the product. The key constraint on formulation is that the product must be virtually anhydrous to prevent the premature dissolution of the gasified solid if used in an aqueous environment, under sable storage conditions otherwise.

The invention of this application is described above both generically, and with regard to specific embodiments. A wide variety of alternatives known to those of ordinary skill in the art can be selected within the generic disclosure, and examples are not to be interpreted as limiting, unless specifically so indicated. The invention is not otherwise limited, except for the recitation of the claims set forth below.

What is claimed is:

1. A composition of matter, comprising a gasified solid and a virtually anhydrous liquid base, wherein said composition is used in an environment where said gasified solid is mechanically abraded or exposed to an aqueous solvent, such that in use, such composition provides a popping sound when said composition is used, said gasified solid comprising a matrix of a water soluble material which encapsulates a gas, said water soluble material being selected from the group consisting of sugar, glucose, lactose and mixtures thereof, and wherein said anhydrous liquid base comprises an agent selected from the group consisting of mineral oils, vegetable oils, petrolatum, liquid fatty acid esters, silicone derivatives, glycerin, propylene glycol, butylene glycol, low molecular weight polyethylene glycol (PEG) and alcohols.

2. The composition of claim 17, further comprising at least one of a surfactant, an emollient, a humectant, a polymer, an enzyme, a builder, an insecticide and a sun screen.

3. The composition of claim 2, wherein said surfactant is selected from the group consisting of sodium cocoyl isethionate, sodium dodecyl benzene sulfonate, sodium methyl oleoyl taurate, sodium lauryl sulfoacetate, sodium lauryl sulfate, sodium $C_{14-16}$ olefin sulfonate, disodium lauryl sulfosuccinate, cocamidopropyl betaine, lauramide MEA, sucrose stearate, cetyl alcohol, laureth-3, polysorbate-85, sorbitan monolaurate, PEG-30 castor oil, PEG-6 cocamide, nonoxynol-9, and distearyl dimethyl ammonium chloride.

4. The composition of claim 1, wherein said emollient is selected from the group consisting of mineral oil vegetable oils, petrolatum, dimethicone, dimethicone copolyols, cyclomethicone, silicone oils and waxes, fatty acid esters and fatty alcohols.

5. The composition of claim 1, wherein said humectant is selected from the group consisting of PEG, glycerin, propylene glycol, sorbitol and sodium lactate.

6. The composition of claim 1, wherein said composition contains water in an amount not more than about 1% by weight.

7. The composition of claim 1, wherein said matrix melts at a temperature below that indicated for use of said composition.

8. The composition of claim 7, wherein said water soluble material is a solid matrix of sugar, glucose and lactose.

9. The composition of claim 1, wherein said composition is in the form of a personal care composition for application to human skin in the presence of water.

10. The composition of claim 1, wherein said composition is in the form of a cleaning agent, and in use is combined with an aqueous solvent and an object to be cleaned.

11. A method of treating human skin, comprising contacting said skin with the composition of claim 1, in the presence of sufficient water or mechanical abrasion to cause said gasified solid to release encapsulated gas.

12. A method of cleaning an object, which comprises combining said object with the composition of claim 1 and an aqueous solvent sufficient to dissolve said gasified solid.

* * * * *

UNITED STATES PATENT AND TRADEMARK OFFICE
CERTIFICATE OF CORRECTION

PATENT NO.    : 6,310,014 B1
DATED         : October 30, 2001
INVENTOR(S)   : Allen H. Rau It is certified that error appears in the above-identified patent and that said Letters Patent is hereby corrected as shown below:

<u>Column 8,</u>
Line 25, "claim 17" should read -- claim 1 --.

Signed and Sealed this

Fourteenth Day of May, 2002

*Attest:*

*Attesting Officer*

JAMES E. ROGAN
*Director of the United States Patent and Trademark Office*